United States Patent [19]

Morrison, Jr. et al.

[11] 4,057,064
[45] Nov. 8, 1977

[54] ELECTROSURGICAL METHOD AND APPARATUS FOR INITIATING AN ELECTRICAL DISCHARGE IN AN INERT GAS FLOW

[75] Inventors: Charles F. Morrison, Jr.; Benson C. Weaver, both of Boulder, Colo.

[73] Assignee: Valleylab, Inc., Boulder, Colo.

[21] Appl. No.: 649,683

[22] Filed: Jan. 16, 1976

[51] Int. Cl.² .............................................. A61B 17/36
[52] U.S. Cl. ............................ 128/303.17; 219/121 P
[58] Field of Search ........... 128/303.1, 303.17, 303.14, 128/303.13, DIG. 22; 219/121 P, 75

[56] References Cited

U.S. PATENT DOCUMENTS

| 2,047,535 | 7/1936 | Wappler | 128/303.17 |
| 3,434,476 | 3/1969 | Shaw et al. | 128/303.1 |
| 3,612,807 | 10/1971 | Liefkens et al. | 219/121 P |
| 3,824,398 | 7/1974 | Boom | 219/121 P X |
| 3,832,513 | 8/1974 | Klasson | 219/121 P X |

OTHER PUBLICATIONS

"R F and Laser Combine to Produce High-Energy Beam", *Machine Design*, Nov. 27, 1975.

*Primary Examiner*—Robert W. Michell
*Assistant Examiner*—Michael H. Thaler
*Attorney, Agent, or Firm*—Gerald J. Ferguson, Jr.; Joseph J. Baker

[57] ABSTRACT

A method and apparatus for initiating an electrical discharge in a formation of flowing inert gas disposed adjacent the end of an electrode by generating charged particles in the vicinity of said inert gas formation. The charged particles may be generated by various means such as an electron emissive filament, a radioactive material or an auxiliary electrical discharge located adjacent to the electrode but removed from the end thereof. The auxiliary electrical discharge may be in electrical series with the electrode and it may be located inside or outside the flow of inert gas needed to establish the gas formation at the end of the electrode.

27 Claims, 8 Drawing Figures

ELECTROSURGICAL METHOD AND APPARATUS FOR INITIATING AN ELECTRICAL DISCHARGE IN AN INERT GAS FLOW

RELATED APPLICATIONS

This application is related to a first U.S. patent application Ser. No. 649,725 filed on Jan. 16, 1976 by Charles F. Morrison, Jr., Frank W. Harris, and Michael C. Patzer, entitled "Electrosurgical Method and Apparatus for Establishing an Electrical Discharge in an Inert Gas Flow" and a second U.S. patent application Ser. No. 649,682 filed on Jan. 16, 1976 by Charles F. Morrison, Jr., entitled "Electrosurgical Method and Apparatus for Initiating an Electrical Discharge in an Inert Gas Flow", all of the foregoing applications being assigned to the same assignee.

BACKGROUND OF THE INVENTION

This invention relates to the initiation of electrical discharges and in particular to the initiation of such discharges in inert gas flows.

In the first of the above-mentioned related patent applications, there is disclosed a method and apparatus for establishing an electrical discharge from an electrode by forming a column of inert gas adjacent the electrode whereby the discharge is both long and directed. There is also disclosed an electrosurgical method and apparatus for coagulating by fulguration where a long electrical discharge is established either through a diffuse blanket of inert gas or a well defined column of the gas. Since the discharge is long, any tendency for the electrode to contact the surface being treated is substantially lessened whereby undesirable sticking of coagulated tissue to the electrode in electrosurgical applications is practically eliminated. However, there is some difficulty in initiating this long electrical discharge and thus, it is necessary to touch the electrode down on or very near to the tissue being coagulated. This can also result in adhesion of tissue to the hot electrode where the tissue can be ripped away when the instrument is removed from the site thereby causing surgical complications. Further, the adhered tissue tends to foul the electrode such that it must be scraped clean before the surgical procedure can continue.

SUMMARY OF THE INVENTION

With this invention, the above difficulties can be totally eliminated. Further, as will be brought out in detail hereinafter, extension of the invention to non-surgical applications such as thermal-inert-gas welding is also advantageous and desirable.

A primary object of this invention is the provision of a method and apparatus for initiating a long electrical discharge in a formation of inert gas.

A further object of this invention is the provision of an electrosurgical method and apparatus for coagulating by fulguration where the electrical discharge is initiated and established either through a diffuse blanket of inert gas or a well defined column of the gas.

These and other objects of the invention will become apparent from a reading of the following specification and claims taken together with the drawing.

DETAILED DESCRIPTION OF THE PREFERRED EMBODIMENTS OF THE INVENTION

Figure 1:
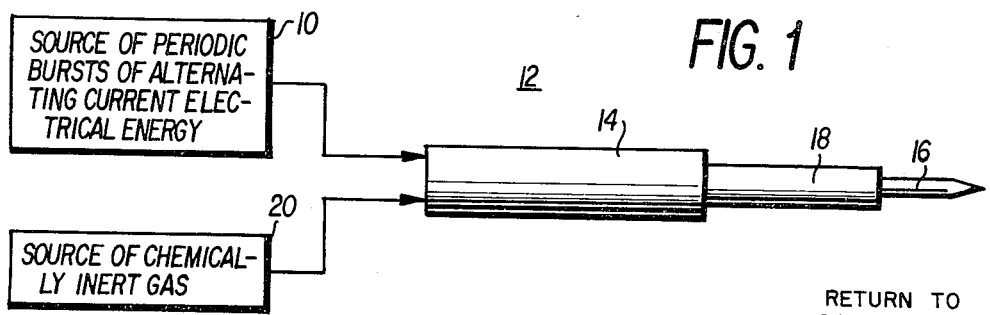
FIG. 1 is an illustrative schematic diagram of apparatus in accordance with the invention.
Figure 7:
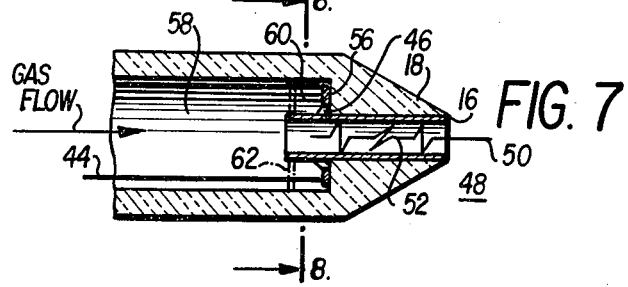

Referring to the figures of the drawing where like reference numerals refer to like parts and, in particular, referring to FIG. 1, there is shown a source 10 of electrical energy which may be continuous or preferably discontinuous such as periodic bursts of electrical energy as illustrated in FIG. 7 of U.S. Pat. No. 3,699,967 granted to Robert K. Anderson. This energy is typically in the high frequency range — that is, about 200 kHz or higher. The waveform has a high crest factor — that is, typically about 5–10 where the crest factor of a periodic function is the ratio of its crest (peak, maximum) value to its root-mean-square value. The bursts may occur at a repetition rate of 15,000 to 50,000 bursts per second while the duration of each burst may consist of 1 to 5 cycles of the high frequency energy, it being understood that none of the foregoing values is critical. Such waveforms are well known for use as coagulating waveforms in electrosurgery. It should be understood that source 10 may also generate waveforms of other types such as those used in thermal-inert-gas (TIG) welding.

Source 10 may be connected to an electrosurgical instrument or a welding instrument generally indicated at 12. Instrument 12 basically comprises a support member 14, which may function as a handle. Member 14 supports an active electrode 16, which may be directly supported by member 14 or indirectly supported thereby via an intermediate member 18, although intermediate member 18 does not necessarily also have to be employed as a support member, as will be described in more detail hereinafter. Source 10 may be electrically connected in a conventional manner to electrode 16 by appropriate connections (not shown) internal to members 14 and 18.

A source 20 of gas is also connected to instrument 12 and, as will be described in more detail hereinafter, the gas is employed to support an electrical discharge used for tissue coagulation and the like. The gas should be inert in the sense that it is not combustible by the electrical discharge nor will it support combustion of the electrode 16. It may, for example, be selected from the group consisting of nitrogen and the noble gases and mixtures thereof. Helium is particularly advantageous as discussed in the first of the before-mentioned related patent applications.

Figure 2:
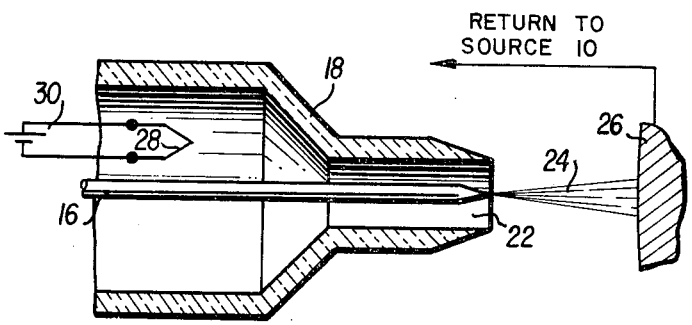
FIGS. 2 and 3 are cross-sectional views of various illustrative electrode structures in accordance with one aspect of the invention wherein auxiliary charged particle generators are employed.

In FIGS. 2–8 there are shown electrode structures generally corresponding to that shown in FIG. 1. In FIG. 2, intermediate member 18 comprises a hollow tube disposed about and surrounding electrode 16 whereby an annular passageway 22 is provided through which the gas from source 20 flows. As the gas flows out of tube 18 an outwardly extending column of flowing inert gas is formed adjacent the tip or end of electrode 16 to thereby facilitate the establishment and maintenance of a highly directive discharge 24 to a surface such as body tissue or the like, although in this application the surface 26 may also be metal or the like as in welding operations or the like. The active electrode is electrically conductive and typically may be made from tungsten, stainless steel, etc., while the tube 18 is preferably made from an electrically insulative material. The radial distance between the forward end of electrode 16 and tube 18 may typically be about 30 mils while the diameter of electrode 16 is typically about 12–15 mils, it being understood that none of the foregoing values are critical to the desired formation of a column of gas.

The outwardly extending column of inert gas is well defined and produces a very long electrical discharge. This discharge is four to six times the length of that generated under the same conditions without the gas. The discharge is straight down the gas column. The directivity of the discharge is such that it can be directed to the bottom of a fissure or crevice without deflecting to the sides thereof.

The directivity and length of the discharge are very desirable; however, there is some difficulty in initiating the discharge and thus, it is necessary to touch the electrode 16 down on or very near to the surface 26. This can result in adhesion of tissue to the hot electrode such that the tissue can be ripped away when the instrument is removed from surface 26, thereby causing surgical complications. Further, the adhered tissue tends to foul the electrode such that it must be scraped clean before the surgical procedure can continue. To avoid these problems discharge initiating means 28 is provided. In FIG. 2, means 28 comprises a hot wire or electron emitting filament disposed in the gas flowing from source 20 through tube 18 where the filament is connected to a potential source 30. In order to more effectively draw the electrons into the flowing gas, a bias potential (not shown) may be applied to electrode 16 where electrode 16 would be positively biased with respect to filament 28.

Although the theory of operation may not be perfectly understood, it is thought that the electrons emitted by filament 28 create ions which are swept by the inert gas through tube 18 to the region in front of the electrode whereby an electrical discharge is initiated in the inert gas assuming an appropriate electrical potential is on active electrode 16 and assuming active electrode 16 is in the electric field of an appropriate return electrode. In electrosurgical applications, the return electrode would typically be the patient's body (surface 26) which is in electrical contact with a return electrode, which preferably has a large area. In welding applications, the return electrode would correspond to an electrically conductive surface such as the workpiece (surface 26) to be welded. When active electrode 16 is substantially removed from surface 26, but still in the field of the return electrode, the electrical discharge initiated by the electrons emitted by filament 28 is a tiny hair line of corona discharge which extends a substantial distance from the active electrode due to the presence of the gas flow. As active electrode 16 is brought closer to surface 26, the electrical discharge becomes heavy and luminous. Typically, the discharge necessary to effect coagulation by fulguration occurs when the active electrode is within about one-half inch of the tissue and hence, no tissue will undesirably adhere to the electrode. As stated above, the foregoing theory of operation may not be perfectly understood and, in any event, there is no intention to be limited thereby. To the extent that the theory is accurate, it also applies to the remaining embodiments of the invention except where noted.

Figure 3:
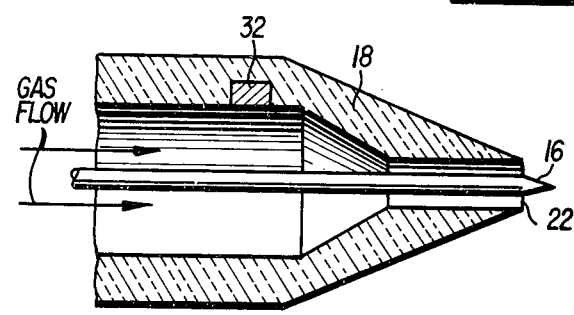
Figure 4:
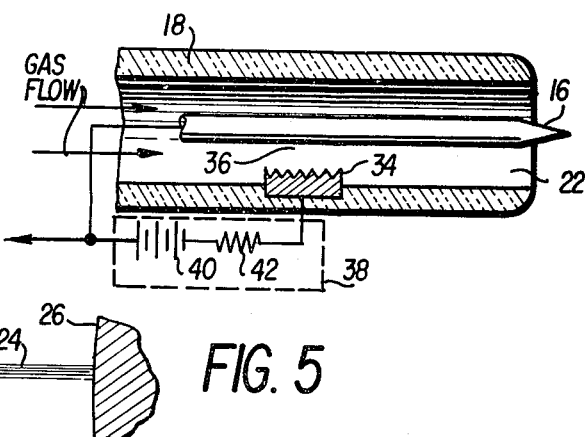
FIGS. 4–7 are cross-sectional views of illustrative electrode structures in accordance with a further aspect of the invention wherein auxiliary electrical discharges are employed.

In FIG. 3, electrically charged particles are generated by a source of radioactive material 32 while in FIG. 4 the charged particles are supplied by an auxiliary electric discharge established between an electrically conductive electrode 34 and a portion of the active electrode, the portion being generally indicated at 36. The location of portion 36 with respect to the tip of electrode 16 is not critical and it need only be removed from the tip to the extent necessary to maintain gas flow integrity. The electrically conductive electrode is electrically biased with respect to the active electrode 16 by a power supply 38 which may comprise a battery 40 and a resistor 42.

In the embodiment of FIGS. 5–8, an auxiliary electrical discharge is established in electrical series connection with active electrode 16. Thus, there is no need for the additional means described in FIGS. 2–4 for providing charged particles. In particular, in FIG. 5, electrical conductor 44 is connected at one end thereof to source 10 of electrical energy. The other end thereof is closely disposed with respect to active electrode 16 so that a gap 46 separates the end of conductor 44, which is of rigid construction at this point, and active electrode 16. The gap should be of sufficient width to insure the ready establishment of a discharge thereacross. Typically the gap width may be 10–20 mils although these values are not critical. Thus, the electrical connection between source 10 and electrode 16 is only by electrical discharge. However, this discharge is much shorter than that between electrode 16 and surface 26. Thus, much less power is lost here than in the longer discharge at surface 26. Once the longer discharge is initiated, means (not shown) may be employed to short gap 46 to thereby avoid the power loss.

Figure 6:
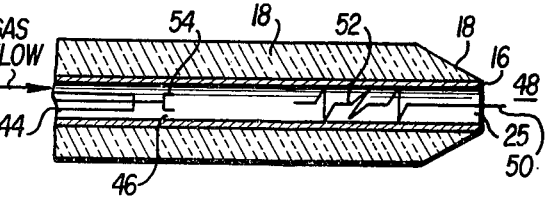

In FIG. 6, the electrode 16 includes a hollow tube having a passageway 25 for inert gas. The tube has an inside diameter of typically 15–60 mils, it being understood that the foregoing values are not critical. Intermediate member 18 comprises a coating disposed on electrode 16 where preferably the coating is made of electrically insulating material. The gas flows through the electrode, cooling it very effectively, while providing a conduction column to surface 26. Active electrode 16 also includes a fine wire electrode 48 made of tungsten or a like material. The wire is bent so its tip or end portion 50 is in substantial alignment with the axis of tube 16 while the remainder 52 thereof is in snug pressing engagement with the interior of tube 16 whereby electrode 48 can be easily removed and replaced if it is badly damaged. Conductor 44 is disposed within tube 16 whereby the auxiliary electrical discharge occurs between electrode structure 54 mounted on conductor 44 and the interior of tube 16.

Figure 5:
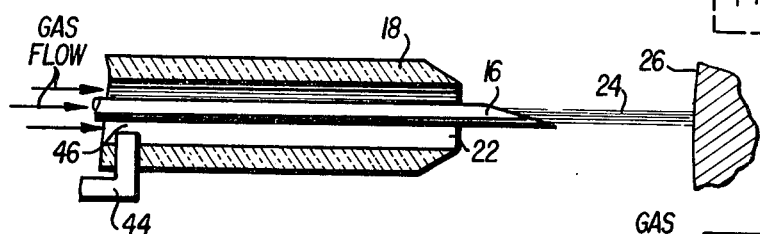
Figure 8:
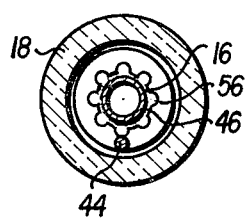
FIG. 8 is a cross-sectional view taken on the line 8—8 of FIG. 7.

In the embodiment of FIGS. 5 and 6, the auxiliary electrical discharge is established in the path of the flowing inert gas whereby the charged particles of the discharge can be swept to the forward end of electrode 16 or 48 to initiate a discharge thereat. In the embodiment of FIGS. 7 and 8, the auxiliary electrical discharge may or may not be in the path of the flowing gas. In fact, the auxiliary electrical discharge may be completely out of the path of the flowing gas and as much as 6 inches away from the electrode tip in any direction from the tip. Thus, the auxiliary discharge merely has to be in the proximity of the tip. In one embodiment, there is provided a "star" washer 56 or the like which is connected to conductor 44 and which surrounds tube 16 whereby gap 46 is formed between the exterior of tube 16 and the internal perimeter of washer 56. As can be seen in FIG. 7, a chamber 58 may be provided into which tube 16 extends. Further, an annular air tight compartment 60 may be optionally formed by mounting a washer 62 (shown in phantom lines) or the like about the outside portion of tube 16, whereby provision would be made for conductor 44 to pass through washer 62 without electrically contacting the washer. If washer 62 is not provided, the charged particles generated in the gap 46 will be in the inert gas flow and the operation would be substantially the same as that described for FIGS. 5 and 6.

However, if washer 62 is employed, the auxiliary discharge established at 46 will nevertheless initiate a discharge at the tip of electrode 48, assuming the other conditions discussed hereinbefore are met for establishing a discharge, even though the charged particles generated by the auxiliary discharge are not swept along by the flowing inert gas to electrode 48. It is thought that the electric field associated with the auxiliary discharge is instrumental in initiating the arc at electrode 48 but once again, it is to be understood that there is no intent to be limited to a particular theory of operation.

What is claimed is:

1. Electrical apparatus for producing coagulation of tissue, said apparatus comprising
   a support;
   a source of electrical energy for effecting the tissue coagulation;
   an active electrode being supported by said support and outwardly extending therefrom for applying said electrical energy to said tissue, there being only one electrical path from said source of electrical energy to said active electrode;
   a source of inert gas;
   gas flow directing means connected to said source of inert gas for directing the gas past said active electrode to thereby facilitate the establishment of a primary electrical discharge in the gas disposed adjacent the end of the active electrode and extending outwardly therefrom;
   discharge initiating means disposed in the proximity of said active electrode for initiating said primary electrical discharge,
   both said active electrode and said discharge initiating means each being responsive, via said electrical path, only to said electrical energy for effecting tissue coagulation; and
   means for returning said electrical energy from said tissue to said source of electrical energy.

2. Apparatus as in claim 1 where said discharge initiating means is located in the gas flow established by said gas flow directing means.

3. Apparatus as in claim 2 where said discharge initiating means include charged particle generating means for generating electrically charged particles.

4. Apparatus as in claim 3 where said charged particle generating means includes first and second auxiliary electrodes having a small gap therebetween, across which an auxiliary electrical discharge is generated so that said auxiliary discharge initiates said primary electrical discharge.

5. Apparatus as in claim 4 where said first auxiliary electrode is a portion of said active electrode, said portion being removed from said end of the electrode.

6. Apparatus as in claim 1 where discharge initiating means is located outside the gas flow established by said gas flow directing means.

7. Apparatus as in claim 6 where said discharge initiating means includes first and second auxiliary electrodes having a small gap therebetween, across which an auxiliary discharge is generated so that said auxiliary discharge initiates said primary electrical discharge.

8. Apparatus for establishing an electrical discharge to an object comprising
   a support;
   a source of electrical energy;
   an active electrode supported by said support and outwardly extending therefrom;
   a source of inert gas;
   gas flow directing means connected to said source of inert gas for directing the gas past said electrode to thereby facilitate the establishment of a primary electrical discharge to said object in the gas disposed adjacent the end of the electrode and extending outwardly therefrom;
   discharge initiating means for initiating said primary electrical discharge, said discharge initiating means including a second electrode connected to said source of electrical energy and so disposed with respect to said active electrode that a gap is formed therebetween, said gap being adapted for the formation of an auxiliary electrical discharge thereacross to thereby initiate said primary electrical discharge and said gap comprising the only path, at least during the initiation of said auxiliary electrical discharge, for the electrical energy to said active electrode; and
   means for returning said electrical energy from said object to said source of electrical energy.

9. Apparatus as in claim 8 where said active electrode comprises a hollow tube and said second electrode is disposed inside of said tube.

10. Apparatus as in claim 8 where said second electrode is annular shaped and disposed about and surrounds said active electrode.

11. Apparatus as in claim 8 where said active electrode comprises a hollow tube and a bent metal wire disposed inside said tube in pressing contact therewith, said bent wire having an end portion in substantial alignment with the axis of said tube.

12. Apparatus as in claim 8 including an electrically insulative tube disposed about said active electrode.

13. An instrument for producing coagulation of tissue comprising
   a support;
   an active electrode supported by said support and outwardly extending therefrom adapted for applying electrical energy to said tissue to effect the coagulation thereof, there being only one electrical path of said electrical energy to said active electrode;
   gas flow directing means adapted for the directing of gas past said electrode to provide gas adjacent the end of said electrode and extending outwardly therefrom; and
   discharge initiating means disposed in the proximity of said electrode adapted for the initiation of a primary electrical discharge in said gas formed adjacent the end of the electrode both said active electrode and said discharge 14. An instrument as in claim 13 where said discharge initiating means is located in the gas flow established by said gas flow.

15. An instrument as in claim 14 where said discharge initiating means includes charged particle generating means for generating electrically charged particles.

16. An instrument as in claim 15 where said charged particle means includes first and second auxiliary electrodes having a small gap therebetween.

17. An instrument as in claim 16 where said first auxiliary electrode is a portion of said active electrode, said portion being removed from said end of the electrode.

18. An instrument as in claim 13 where discharge initiating means is located outside the gas flow established by said gas flow directing means.

19. An instrument as in claim 18 where said discharge initiating means includes first and second auxiliary electrodes having a small gap therebetween, across which an auxiliary discharge is generated so that said auxiliary discharge initiates said primary electrical discharge.

20. An instrument comprising
a support;
an active electrode supported by said support and outwardly extending therefrom;
gas flow directing means adapted for the directing of gas past said electrode to provide gas adjacent the end of said electrode and extending outwardly therefrom; and
discharge initiating means disposed in the proximity of said electrode adapted for the initiation of a primary electrical discharge in said gas formed adjacent the end of the electrode, said discharge initiating means including a second electrode so disposed with respect to said active electrode that a gap is formed therebetween, said gap being adapted for the formation of an auxiliary electrical discharge thereacross to thereby initiate said primary electrical discharge and said gap comprising the only path, at least during the initiation of said auxiliary electrical discharge, for the electrical energy to said active electrode.

21. An instrument as in claim 20 where said active electrode comprises a hollow tube and said second electrode is disposed inside of said tube.

22. An instrument as in claim 20 where said second electrode is annular shaped and disposed about and surrounds said active electrode.

23. An instrument as in claim 20 where said active electrode comprises a hollow tube and a bent metal wire disposed inside said tube in pressing contact therewith, said bent wire having an end portion in substantial alignment with the axis of said tube.

24. A method for establishing an electrical discharge with an instrument comprising a support, and an active electrode supported by said support and outwardly extending therefrom, said method comprising the performance of the following steps in any desired order,
directing inert gas past said active electrode and outwardly therefrom;
applying electrical energy to said electrode; and
generating an auxiliary electrical discharge at a location removed from the end of said active electrode so that said auxiliary electrical discharge will initiate a primary electrical discharge from said active electrode, said auxiliary electrical discharge being the only path for said electrical energy to said active electrode, at least during the initiation of said auxiliary electrical discharge; and
positioning said active electrode adjacent a body whereby said primary electrical discharge can be initiated without having to bring said active electrode into substantial contact with said body.

25. A method as in claim 24 where said body comprises living organic tissue and said electrical discharge effects coagulation of said tissue by fulguration.

26. A method as in claim 25 where said electrical energy is in the form of periodic bursts of high frequency electrical current.

27. A method as in claim 24 where said body is metallic and said electrical discharge effects welding thereof.

* * * * *